United States Patent [19]

Castoe et al.

[11] 4,235,613
[45] Nov. 25, 1980

[54] PREPARATION OF SALES GAS

[75] Inventors: Alonzo R. Castoe, Irving, Tex.; Jan W. Bass, Monrovia, Calif.

[73] Assignee: Atlantic Richfield Company, Los Angeles, Calif.

[21] Appl. No.: 43,578

[22] Filed: May 29, 1979

Related U.S. Application Data

[63] Continuation-in-part of Ser. No. 918,183, Jun. 22, 1978, abandoned.

[51] Int. Cl.³ ............................................. F25J 3/02
[52] U.S. Cl. ........................................ 62/17; 62/24; 62/28; 55/68
[58] Field of Search ............... 55/48, 44, 68, 73, 88, 55/89; 62/17, 24, 27, 28

[56] References Cited

U.S. PATENT DOCUMENTS

| 3,130,026 | 4/1964 | Becker | 62/17 |
| 3,595,782 | 7/1971 | Bucklin et al. | 55/68 |
| 3,724,226 | 4/1973 | Pachaly | 62/28 |
| 3,770,622 | 11/1973 | Freireich et al. | 55/68 |
| 4,012,212 | 3/1977 | Kniel | 62/28 |

Primary Examiner—Norman Yudkoff
Attorney, Agent, or Firm—Ronnie D. Wilson

[57] ABSTRACT

Method for preparing natural gas having a high carbon dioxide, ethane and propane content to meet sales gas specifications, such as BTU requirements. The gas is prepared by cooling, followed by contacting with at least one physical solvent which has a greater affinity for heavier hydrocarbons and carbon dioxide than for methane, ethane, propane and butane. Ethane, propane and butane separated by the initial cooling are selectively recombined with the gas after solvent contact.

4 Claims, 1 Drawing Figure

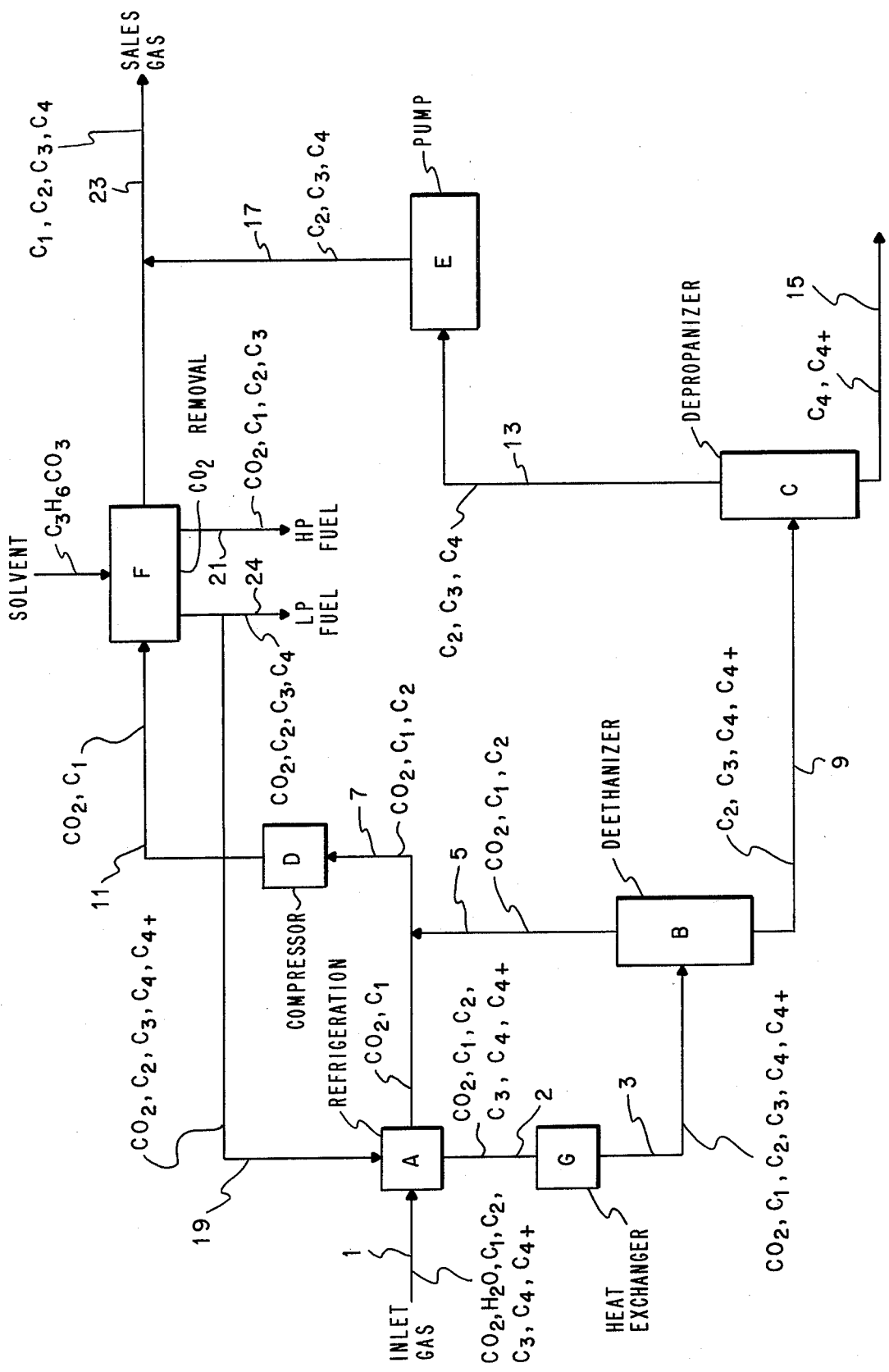

PREPARATION OF SALES GAS

CROSS REFERENCE TO RELATED APPLICATIONS

This application is a continuation-in-part of copending application Ser. No. 918,183, filed June 22, 1978, now abandoned, filed by the same inventors and owned by a common assignee.

This invention is concerned with the treatment of natural gas mixtures. More particularly, the invention is concerned with a method of treating wet natural gas mixtures by which $CO_2$, and hydrocarbons heavier than butanes are separated from the $C_1$ to $C_4$ hydrocarbons to meet sales gas specifications, such as BTU requirements.

Natural gas is a mixture of hydrocarbons, including methane, ethane, propane and various amounts of higher molecular weight hydrocarbons together with acid gases, such as $CO_2$ and/or $H_2S$. A "dry" gas is one containing predominantly methane with some ethane, propane and butane with a very low hydrocarbon dew point. The heavier the hydrocarbons, such as pentane and higher homologs, present in the gas, the higher the hydrocarbon dew point. For pipeline transmission enough of the heavier hydrocarbons must be removed to lower the dew point without losing BTUs to meet specifications. In the past, gas with large quantities of high molecular weight hydrocarbons have been passed through gasoline extraction plants and/or dew point control stations to lower the dew point. Also, frequently the gas has required conditioning to remove sulfur compounds and carbon dioxide. Gas coming from the wellhead usually is saturated with water, which must be removed to prevent formation of ice and hydrates or the accumulation of water which can block the flow as well as cause corrosion.

Natural gas has for years been satisfying a large percentage of the energy needs of this country. Recent economic and political developments have increased the cost of energy sources, such as natural gas. Because of the increased prices for natural gas and the potential shortages thereof, alternative sources of energy have been investigated. The cost of recovering the alternative sources of energy has put much pressure on conserving conventional energy sources, such as natural gas, and utilizing all of the energy contained therein. Therefore, it is needed to recover and utilize the full value of natural gas; whereas, in the past, methods for treating natural gas to bring it to a form commercially usable did not concentrate on its full value but only the easily recovered valuable components thereof. Present day situations are such that all components of natural gas have been and shall continue to become increasingly valuable.

Therefore, there is needed methods for recovering the full value of the various components of natural gas at the lowest possible cost and the utilization of same.

Therefore, it is an object of the present invention to provide a novel integrated process for the preparation of natural gas to meet sales gas specifications.

It is a further object of the present invention to provide a novel integrated process for the preparation of natural gas having a high carbon dioxide, methane, ethane and propane content to meet sales gas specifications.

It is a further object of the present invention to provide a novel integrated process for the preparation of natural gas having a high carbon dioxide, methane, ethane and propane content and containing heavier hydrocarbons, to meet sales gas specifications.

An additional object of the present invention is to provide a novel integrated process for the preparation of natural gas having a high carbon dioxide, methane, ethane and propane content and containing heavier hydrocarbons, to meet sales gas specifications using known physical reactions to achieve the desired results.

Further objects and advantages of the present invention will become apparent to those skilled in the art upon reading the following detailed description and examples.

The present invention provides a method for the preparation of natural gas having a high $CO_2$, methane, ethane and propane content and containing heavier hydrocarbons, to meet sales gas specifications which comprises: (a) separating the gas into a liquid portion of predominantly ethane, propane and heavier hydrocarbons and a gaseous portion predominantly of methane and $CO_2$; (b) fractionating the liquid portion of (a) to yield a gaseous portion of some ethane but predominantly methane and $CO_2$, and a liquid portion of some ethane but predominantly propane and heavier hydrocarbons; (c) fractionating the liquid portion from (b) to yield a gaseous portion of predominantly ethane, propane, and butane and a liquid portion of predominantly heavier hydrocarbons; (d) combining the gaseous portion of (a) and (b) and contacting same with at least one physical solvent which has greater affinity for $CO_2$ and heavier hydrocarbons than methane, ethane and propane; (e) recovering the gaseous hydrocarbons not sorbed by the physical solvent of (d); (f) combining the gaseous portion of (c) with the gas of (e) to provide a sales gas which meets specifications; and (g) recovering the sorbed hydrocarbons in (d) from the solvent and recycling a portion of them to step (a).

The FIGURE shows a block flow diagram according to this invention for preparing natural gas to meet sales gas specifications.

More specifically, the FIGURE shows a source of pressurizied gas containing methane, ethane, propane, butane, heavier hydrocarbons, water and carbon dioxide in pipeline 1 which passes to refrigeration unit A. Refrigeration unit A separates the source gas into a liquid portion of predominantly ethane, propane and heavier hydrocarbons and a gaseous portion predominantly of methane, and $CO_2$. The liquid portion from refrigeration unit A passes via pipe 2 through heat exchanger G to deethanizer B via pipe 3. The gaseous portion of refrigeration unit A passes via pipe 7 to compressor D wherein it is compressed to the desired operating pressure of the $CO_2$ removal unit F.

In deethanizer B the liquid entering via pipe 3 is separated into a gaseous portion of some ethane but predominantly methane and $CO_2$ and a liquid portion of some ethane, but predominantly propane and heavier hydrocarbons. The liquid portion from deethanizer B passes via pipe 9 to depropanizer C. The gaseous portion from deethanizer B passes via pipe 5 to pipe 7 where it is combined with the gaseous portion from unit A. The combined gas from unit A and deethanizer B pass via pipe 7 through compressor D and pipe 11 to $CO_2$ removal unit F.

In $CO_2$ removal unit F the gas fed to it is contacted with at least one physical solvent, having a greater affinity for $CO_2$ and heavier hydrocarbons than methane, ethane and propane.

In depropanizer C the liquid entering via pipe 9 is separated into a gaseous portion of predominantly ethane, propane and butane and a liquid portion of predominantly heavier hydrocarbons. It should be noted that both the gaseous and liquid portions exiting depropanizer C contain some $C_3$ and $C_4$ hydrocarbons. The exact amount of $C_3$ and $C_4$ hydrocarbons in each portion is determined by the sales gas specifications to be met in a given situation. The liquid portion from depropanizer C passes via pipe 15 to wherever it is needed in a given operation, i.e. liquid disposal such as an oil pipeline. The gaseous portion from depropanizer C passes via pipe 13 through pump E and pipe 17 and is combined in pipe 23 with gas exiting from $CO_2$ removal unit F. The combined gas is carried via pipe 23 to a gas pipeline.

The solvent employed in the $CO_2$ removal unit of the present invention is utilized not only to remove carbon dioxide from the gas but also to remove heavier hydrocarbons and water so that the gas can meet requirements for both hydrocarbon dew point and water dew point. There are a substantial number of commercially available physical solvents which have an affinity for heavier hydrocarbons, water and carbon dioxide greater than their affinity for methane, ethane, propane and butane and all of these physical solvents are operable in this invention. Because there are a wide number of physical solvents commercially available for use in the method of this invention, because these physical solvents vary widely as to chemical composition, because varying amounts of different heavier hydrocarbons, carbon dioxide, and water may be sorbed by different physical solvents acting on different gas streams, it is substantially impossible to give pressure and temperature limits for the regeneration of the physical solvent. This is particularly so since combination of two or more gases may be desirably removed together rather than separately. However, a series of heating and/or flash steps, not shown in the diagram, can be employed to regenerate any given physical solvent. Suitable physical solvents known in the art and commercially available include acetone, propylene carbonate, dimethylether of polyethylene glycol, n-methyl-2-pyrrolidone, methanol and methyl-cyanoacetate.

It should be noted that the invention of the present application is viable with natural gas containing near pipeline quality, i.e. 1 to 2 gr/100SCF, of hydrogen sulfide. Natural gas containing greater amounts of $H_2S$ would require additional steps in the physical solvent regeneration. Selection of the physical solvent becomes more critical when greater concentrations of $H_2S$ are present.

EXAMPLE

Inlet natural gas containing 73 mol percent $C_1$, 7 mol percent $C_2$, 3.5 mol percent $C_3$ hydrocarbons, 3 mol percent $C_4$ and heavier ($C_4+$) hydrocarbons, and 13 mol percent carbon dioxide is processed in the flow scheme in the diagram. The temperature and pressure on the inlet gas in pipe 1 is about 98° F. and 475 psia and is reduced to about $-35°$ F. and 450 psia in mechanical refrigeration unit A. $C_2$ and heavier hydrocarbons are removed as liquid via pipe 2 and passed through heat exchanger G to recover refrigeration and achieve a temperature of about 124° F. for entrance to deethanizer B. Pipe 7, carries $C_1$ hydrocarbons and $CO_2$ gas from unit A. Deethanizer B separates the liquid entering into a gaseous portion of $C_1$, $CO_2$, $C_2$ and a liquid portion of $C_2$, $C_3$, $C_4$, and $C_4+$ hydrocarbons. Liquid portion from deethanizer B passes via pipe 9 to depropanizer C. Gaseous portion from Deethanizer B passes via pipe 5 to pipe 7 where it combines with the gaseous portion from unit A.

The combined gases in pipe 7 pass through compressor D and are elevated to a sales gas pipeline pressure of about 1000 psia. Via pipe 11 the gas from compressor D goes to $CO_2$ removal unit F. Pipe 11 gas contains 77 mol percent $C_1$, 7 mol percent $C_2$ and 2 mol percent $C_3$ hydrocarbons, 0.3 mol percent $C_4$ and heavier ($C_4+$) hydrocarbons and 13 mol percent CO .

In the $CO_2$ removal unit F, which utilizes a physical solvent of propylene carbonate, $CO_2$ is removed from the entering gas by a process described in U.S. Pat. No. 2,926,751. The gaseous hydrocarbons not sorbed by the physical solvent are exited from unit F via pipe 23. The high pressure flash gases with light hydrocarbons (predominantly $C_1$, $CO_2$, $C_2$ and $C_3$) exit $CO_2$ removal unit F via pipe 21 and are recovered for use as fuel in the facility. Low pressure flash gases with heavier hydrocarbons (predominantly $CO_2$, $C_2$, $C_3$, and $C_4+$) sorbed by the solvent are recovered from unit F via pipe 24 for use as low pressure fuel, as required, with any excess recycled via pipe 19 and sent to unit A for reprocessing.

Depropanizer C takes the liquid entering via pipe 9 and separates it into a gaseous portion of $C_2$, $C_3$ and some $C_4$ hydrocarbons and a liquid portion of some $C_4$ hydrocarbons and the heavier ($C_4+$) hydrocarbons. The liquid portion from depropanizer C passes via pipe 15 for use in a nearby oil pipeline. The liquid exiting depropanizer C via pipe 15 contains 0.90 mol percent $C_3$ hydrocarbons and 99 mol percent $C_4$ and heavier ($C_4+$) hydrocarbons. The gaseous portion exiting depropanizer C is condensed and passed via pipe 13 through pump E and via line 17 combines in pipe 23 with gas exiting $CO_2$ removal unit F. The combined gas is carried via pipe 23 to a sales gas pipeline. The gas to the sales gas pipeline has a hydrocarbon dew point of below 0° F., water dew point of below $-20°$ F. and contains less than 1% by volume $CO_2$ and about 98% by volume $C_1$, $C_2$, $C_3$, and $C_4$ hydrocarbons.

Reasonable variations and modifications are possible within the scope of this disclosure without departing from the spirit and scope of this invention.

We claim:

1. A method for preparing a wet gas stream of high carbon dioxide, methane, ethane and propane content containing heavier hydrocarbons to meet specifications, which comprises in combination the steps of:
    (a) cooling said gas stream to split same into a liquid portion of predominantly ethane, propane, butane and heavier hydrocarbons and a gaseous portion of predominantly methane and carbon dioxide;
    (b) fractionating said liquid portion from (a) to yield a gaseous portion of predominantly methane and carbon dioxide and a liquid portion of predominantly ethane, propane, butane and heavier hydrocarbons;
    (c) fractionating said liquid portion from (b) to yield a gaseous portion of predominantly ethane, propane, and butane and a liquid portion of predominantly heavier hydrocarbons;
    (d) combining the gaseous portion of (a) and (b) and contacting same with at least one physical solvent which has greater absorbing affinity for carbon dioxide and heavier hydrocarbons than methane, ethane, propane, and butane;

(e) recovering the gaseous hydrocarbons not sorbed by the physical solvent in (d);

(f) combining the gaseous portion of (c) with the recovered gaseous hydrocarbons of (e) to provide a sales gas which meets specifications; and (g) recovering said sorbed hydrocarbons in (d) from said physical solvent and recycling a portion of same to step (a).

2. The method of claim 1 wherein said physical solvent is selected from the group consisting of acetone, propylene carbonate, dimethylether of polyethylene glycol, n-methyl-2-pyrrolidone, methanol and methylcyanoacetate.

3. The method of claim 1 wherein said well gas stream contains at least 5 mol percent carbon dioxide.

4. The method of claim 1 wherein the remaining portion of said recovered sorbed hydrocarbons in step (g) is utilized as facility fuel.

* * * * *